(12) United States Patent
Futagawa et al.

(10) Patent No.: US 9,689,837 B2
(45) Date of Patent: Jun. 27, 2017

(54) DEVICE FOR MEASURING OXIDATION-REDUCTION POTENTIAL AND METHOD FOR MEASURING OXIDATION-REDUCTION POTENTIAL

(71) Applicant: National University Corporation Toyohashi University of Technology, Toyohashi-shi, Aichi (JP)

(72) Inventors: Masato Futagawa, Toyohashi (JP); Kazuaki Sawada, Toyohashi (JP); Sou Takahashi, Toyohashi (JP)

(73) Assignee: National University Corporation Toyohashi University of Technology (JP)

( * ) Notice: Subject to any disclaimer, the term of this patent is extended or adjusted under 35 U.S.C. 154(b) by 263 days.

(21) Appl. No.: 14/419,453

(22) PCT Filed: Aug. 9, 2013

(86) PCT No.: PCT/JP2013/071723
§ 371 (c)(1),
(2) Date: Feb. 3, 2015

(87) PCT Pub. No.: WO2014/025044
PCT Pub. Date: Feb. 13, 2014

(65) Prior Publication Data
US 2015/0226701 A1  Aug. 13, 2015

(30) Foreign Application Priority Data
Aug. 10, 2012 (JP) .................................. 2012-177909

(51) Int. Cl.
*G01N 27/403* (2006.01)
*G01N 27/416* (2006.01)
(Continued)

(52) U.S. Cl.
CPC ......... *G01N 27/4168* (2013.01); *H01L 29/40* (2013.01); *H01L 29/73* (2013.01);
(Continued)

(58) Field of Classification Search
CPC ............. G01N 27/3274; G01N 27/333; G01N 27/403; G01N 27/413; G01N 27/4161
See application file for complete search history.

(56) References Cited

U.S. PATENT DOCUMENTS 5,218,304 A * 6/1993 Kinlen ............... G01N 27/4166
204/412
6,255,678 B1  7/2001 Sawada et al.
(Continued)

FOREIGN PATENT DOCUMENTS

JP   143356/1985      9/1985
JP   10-332423 A     12/1998
(Continued)

OTHER PUBLICATIONS

Entry for "Bipolar Transistor" downloaded on Dec. 21, 2016 from the Electronics Tutorials website http://www.electronics-tutorials. ws/transistor/tran_1.html, twelve pages.*
(Continued)

*Primary Examiner* — Alexander Noguerola
(74) *Attorney, Agent, or Firm* — Quarles & Brady LLP; Gavin J. Milczarek-Desai

(57) ABSTRACT

Provided is a small-sized device for measuring an oxidation-reduction potential, whereby an oxidation-reduction current and an oxidation-reduction potential can be measured by reducing noise even when a signal from a solution being measured is small. A device for measuring an oxidation-reduction potential is provided with a substrate (10), a working electrode (15) mounted on a surface of the substrate (10), and a bipolar transistor (21) for amplifying the output (Continued)

of the working electrode (15) also provided on the surface of the substrate (10), and the signal amplified by the bipolar transistor (21) is inputted to a processing circuit (18).

7 Claims, 15 Drawing Sheets

(51) Int. Cl.
*H01L 29/40* (2006.01)
*H01L 29/73* (2006.01)
*H01L 29/423* (2006.01)
*H01L 29/735* (2006.01)
*H01L 29/10* (2006.01)
*H01L 29/861* (2006.01)
*H01L 27/06* (2006.01)

(52) U.S. Cl.
CPC ...... *H01L 27/0664* (2013.01); *H01L 29/1008* (2013.01); *H01L 29/42304* (2013.01); *H01L 29/735* (2013.01); *H01L 29/8611* (2013.01)

(56) References Cited

U.S. PATENT DOCUMENTS

| | | | |
|---|---|---|---|
| 2004/0063152 A1* | 4/2004 | Gumbrecht | G01N 27/3277 435/7.1 |
| 2005/0258038 A1 | 11/2005 | Harima | |

FOREIGN PATENT DOCUMENTS

| | | |
|---|---|---|
| JP | 2004-514890 A | 5/2004 |
| JP | 2005-331454 A | 12/2005 |
| JP | 2007-33344 A | 2/2007 |

OTHER PUBLICATIONS

International Search Report for PCT/JP2013/071723, with English Translation.
Written Opinion for PCT/JP2013/071723, with English Translation.

\* cited by examiner

Measurement circuit with electrodes alone

Measurement circuit with electrodes and bipolar transistor

Measurement circuit with electrodes, bipolar transistor and diode

Measurement circuit with electrodes and diodes

Measurement with electrodes alone

Measurement with electrodes and bipolar transistor

Measurement with electrodes, bipolar transistor and diode

Measurement with electrodes and diodes

Measurement with electrodes alone

Measurement with electrodes, bipolar transistor and diode

Measurement circuit to measure reduction current only

Measurement circuit to measure oxidation current and reduction current separately Measurement circuit for amplifying and measuring oxidation current and reduction current separately Ep: Type of the substance (Oxidation-reduction potential)

Ip: Concentration of the substance

DEVICE FOR MEASURING OXIDATION-REDUCTION POTENTIAL AND METHOD FOR MEASURING OXIDATION-REDUCTION POTENTIAL

TECHNICAL FIELD

The present invention relates to a device and a method for measuring oxidation-reduction potential used for measuring concentration of a substance in a solution to specify the substance.

BACKGROUND ART

The device for measuring oxidation-reduction potential (ORP) is also known as "redox sensor". "Redox" is a composite word of "reduction" and "oxidation".

Here, reduction refers to a chemical reaction wherein a substance receives electrons, and oxidation refers to a chemical reaction wherein a substance loses electrons. As electrons are released or accepted in oxidation reduction reactions, oxidation and reduction currents flow by electron transfer.

The ORP (or redox potential) is the potential produced when electrons are released or accepted in an oxidation-reduction reaction, and can be used as a measure for the tendency of a substance to release or accept electrons. The ORP is determined by the number of electrons, configuration, and number of ligands of each substance and can be used as an indicator for identifying the substance.

The concentration of a substance in a solution can be determined by measuring oxidation current and reduction current in the solution with the use of the ORP measuring device, as mentioned above. Using the ORP measuring device, the substance in the solution can be identified and the oxidation-reduction reaction can be clarified, based on the ORP determined from the oxidation current and reduction current.

The conventional ORP measuring device for measuring the concentration of a substance in a solution to identify the substance includes an element that carries measurement electrodes for measuring the oxidation current and reduction current of the solution, and an element that carries a processing circuit for processing the obtained oxidation and reduction current signals. These elements are separate, and the measurement electrodes and the processing circuit are connected to each other via wiring.

Generally, the measurement electrodes of the ORP measuring device are made up of a working electrode, a counter electrode, and a reference electrode. The oxidation and reduction currents flow between the working electrode and the counter electrode. The oxidation and reduction current signals are processed by the processing circuit to determine the concentration of the substance in the solution, and the substance is thus specified.

ORP measuring devices are used for research and applications of various chemical reactions including bioreactions in a variety of fields such as agricultural, medical, and environmental fields.

SUMMARY OF INVENTION

Technical Problem

In measuring oxidation and reduction currents with the use of a conventional ORP measuring device, reduction in size of the working electrode for accurate measurement of a minute measured object weakens the measured signals of the oxidation and reduction currents. If the concentration of the solution being measured is lowered, the measured signals of oxidation and reduction currents are also reduced.

As the measured signals are weakened, they are affected largely by noise from external sources, which compromises the reliability of the measurement results.

In some fields such as medical, agricultural, and zootechnical fields, in particular, attempts are being made to perform treatment or achieve management of fertilizers for plants and livestock farming based on observation of cells and living tissues as small as several microns or less. This has necessitated reduction in size of the working electrode for precise measurement with the use of an ORP measuring device. Therefore, it is desired to measure a current signal of several picoamperes or less, for example, in a noiseless manner, despite the lowered intensity of measured signal because of the size reduction of the working electrode.

Solution to Problem

A first aspect of this invention is defined as follows: a device for measuring oxidation-reduction potential, including:
a substrate;
a working electrode formed on a surface of the substrate; and
a processing circuit that processes an output of the working electrode;
wherein the substrate is provided with a bipolar transistor for amplifying the output of the working electrode.

In the ORP measuring device according to the first aspect as defined above, since a bipolar transistor is provided on the same substrate as the working electrode, the output (current) from the working electrode is amplified by the bipolar transistor before noise is added thereto. The amplified output from the working electrode is therefore less susceptible to noise and thereby the reliability of the measurement results is improved.

In a configuration wherein the output of the working electrode is input to the bipolar transistor, the rectifying function of the bipolar transistor affects. For example, let us consider a circuit in which the current from the working electrode is output to the base of the bipolar transistor when a first potential is applied to the counter electrode. At this time, an oxidation reaction (or reduction reaction) is taking place at the object being measured at the first potential. When a second potential that will cause a reaction different from that by the first potential (reduction reaction or oxidation reaction) is applied to the counter electrode in this circuit, the current tries to flow to the working electrode but does not flow, because the bipolar transistor is connected. Therefore, if such ORP measurement is repeatedly conducted, only the oxidation reaction (or reduction reaction) will progress, which may eventually disturb the ion balance of the measured object (solution).

Therefore, in a second aspect of the invention, in the measuring device defined in the first aspect, a compensation circuit is further provided, which applies a compensation current to the working electrode in a direction opposite to that of a current applied from the working electrode to the bipolar transistor.

This compensation current allows both the oxidation reaction and the reduction reaction to always occur at the measured object during the measurement of ORP.

The compensation current conducting to the working electrode can be supplied by arranging a rectifying semiconductor such as a diode or a bipolar transistor in parallel with the bipolar transistor between the working electrode and the processing circuit (fourth aspect).

The current can also be supplied by connecting a constant current circuit or a constant voltage circuit between the working electrode and the base of the bipolar transistor.

When connecting a constant current circuit or a constant voltage circuit, it is preferable to shift the current applied from the working electrode to the bipolar transistor. Namely, if the bipolar transistor is an NPN type, current is applied in the positive direction, whereas if the bipolar transistor is a PNP type, current is applied in the negative direction, so that the current applied to the base of the bipolar transistor is in a range in which the amplification factor of the bipolar transistor is constant.

The "range in which the amplification factor of the bipolar transistor is constant" here means a range of amplification factor in which the output waveform (current-voltage) of the working electrode during the ORP measurement will not be deformed, in other words, the range of amplification factor in which the similar shape of the output waveform is maintained. The "similar shape of the waveform" refers to a waveform that can become substantially congruent to the original waveform in a current-voltage characteristics chart by adjusting the scale of the current, in particular.

The current that causes the current applied from the working electrode to the base of the bipolar transistor to be shifted is referred to as "shift current".

When the amplification factor of the bipolar transistor is maintained constant by applying such a shift current, the waveform of the output of the working electrode is hardly distorted.

A sixth aspect of this invention is defined as follows: The measuring device as described above, wherein a first doped region doped to be a first conductor type to form a collector region of the bipolar transistor, a second doped region doped to be a second conductor type within the first doped region to form a base region of the bipolar transistor, and a third doped region doped to be the first conductor type within the second doped region to form an emitter region of the bipolar transistor are formed on the substrate, and wherein the working electrode is stacked upon the base region exposed on a surface of the substrate.

In the ORP measuring device according to the sixth aspect defined as above, since the working electrode and the bipolar transistor are formed integrally, the wiring for connecting the working electrode and the bipolar transistor is omitted. Therefore, noise from an external source can be reduced even more reliably.

An ORP measurement method according to a seventh aspect of this invention is defined as follows: a method of measuring oxidation-reduction potential that uses a measuring device including a substrate, a working electrode arranged in a container formed on a surface of the substrate, a processing circuit that processes an output of the working electrode, and a bipolar transistor formed on the substrate to amplify the output of the working electrode, the measurement method including the steps of:

sweeping voltage applied to a counter electrode arranged opposite to the working electrode inside the container;

amplifying a current output from the working electrode with the bipolar transistor before the current is applied to the processing circuit; and producing a compensation current that flows in a direction opposite to that of a current output from the working electrode to a base of the bipolar transistor in a case where a first potential is applied to the counter electrode, when a second potential different from the first potential is applied to the counter electrode.

The ORP measurement method according to the seventh aspect defined as above provides the same effects as the first aspect.

A measurement method according to an eighth aspect of this invention is defined as follows: In the measurement method defined according to the seventh aspect, a shifting current is applied to the current output from the working electrode to the base of the bipolar transistor so that the bipolar transistor has a constant amplification factor.

The measurement method according to the eighth aspect defined as above provides the same effects as the third aspect.

DESCRIPTION OF EMBODIMENT

Figure 1:
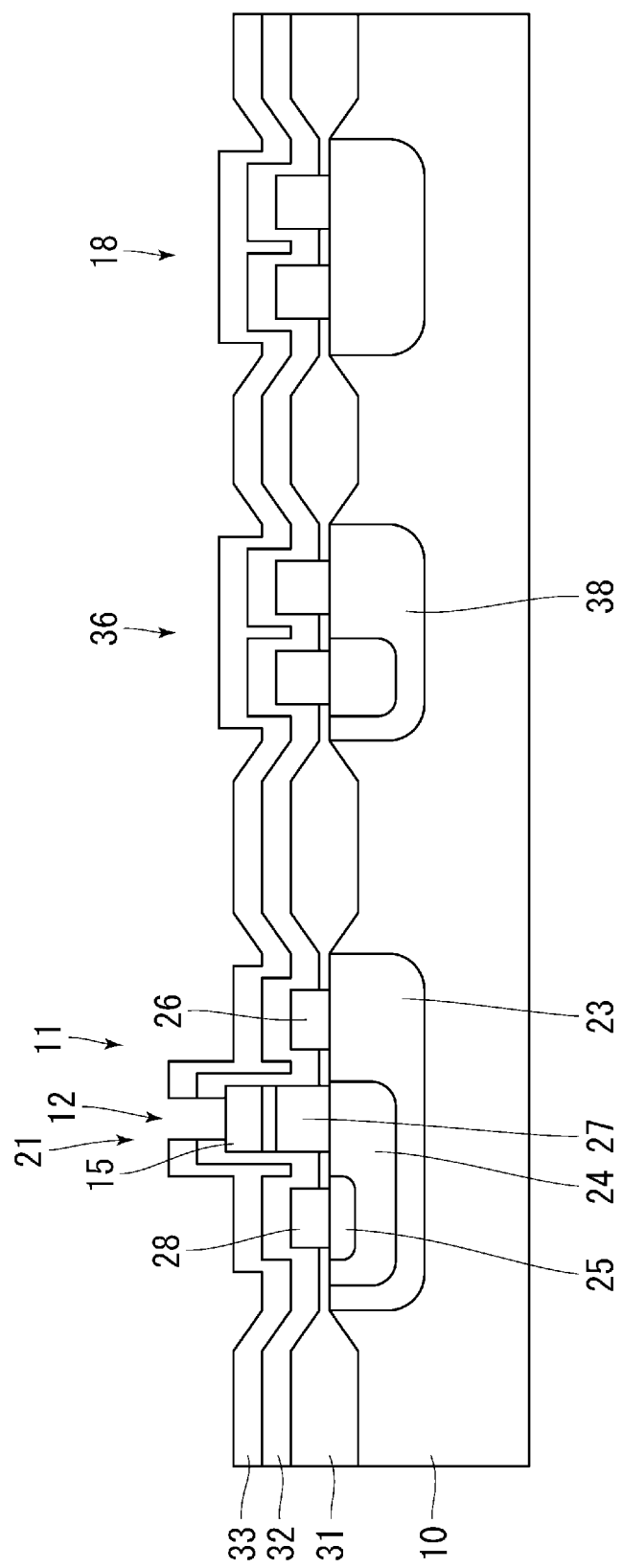
FIG. 1 is a cross-sectional view illustrating an ORP (Oxidation-Reduction Potential) measuring device according to an embodiment of the present invention.

FIG. 1 shows an ORP (Oxidation-Reduction Potential) measuring device according to an embodiment of the present invention. This measuring device includes a substrate 10, and a measurement unit 11 and a signal processing circuit 18 that are formed on the substrate 10. The measurement unit 11 includes a container 12 formed on a surface of the substrate to pour in a solution to be measured, and a working electrode 15, a counter electrode, and a reference electrode that are set in the container 12. The signal processing circuit 18 processes output signals from the working electrode 15. The measuring device includes a bipolar transistor 21 that amplifies output signals from the working electrode 15 and outputs the signals to the signal processing circuit 18. In FIG. 1, the counter electrode and reference electrode are not shown.

The measuring device of FIG. 1 will be described further. Formed on the substrate 10 are a first doped region doped to be a first conductor type to form a collector region 23 of the bipolar transistor 21, a second doped region doped to be a second conductor type within the first doped region to form a base region 24 of the bipolar transistor 21, and a third doped region doped to be the first conductor type within the second doped region to form an emitter region 25 of the bipolar transistor. A collector electrode 26 is formed on the collector region 23, a base electrode 27 is formed on the base region 24, and an emitter electrode 28 is formed on the emitter region 25. The working electrode 15 is formed integrally with the base electrode 27 on the base electrode 27.

The working electrode 15 and the base electrode 27 may be separate components, but it is preferable to stack the working electrode 15 directly or via another conductive layer on the base electrode 27. In other words, the base electrode 27 is electrically connected to the working electrode 15 without wiring.

A silicon substrate is used as the substrate 10, but the substrate 10 is not limited to a silicon substrate. If a silicon substrate is used as the substrate 10, for example, a silicon thermal oxide film 31 is formed on the surface of the substrate 10 for separation of the elements from each other. A silicon plasma oxide film 32 is formed by plasma CVD on the silicon thermal oxide film to reduce distortion. A silicon nitride film 33 is formed on the silicon plasma oxide film 32. The collector electrode 26, base electrode 27, and emitter electrode 28 are made of aluminum, for example. A titanium layer is formed on the base electrode 27 made of aluminum, and the working electrode 15 is made from any of platinum, carbon, or gold on the titanium layer.

While the working electrode and processing circuit are formed on separate substrates in the conventional ORP measuring device, the ORP measuring device of the present invention can have the working electrode and processing circuit formed on the same substrate.

Also, since the bipolar transistor used in the ORP measuring device of the present invention is a current amplifying element that efficiently amplifies current, it is hardly affected by noise.

With the working electrode and processing circuit formed on the same substrate, the wiring connecting the working electrode and processing circuit is shortened, so that noise from the wiring to the processing circuit can be reduced. This enables accurate measurement of very small oxidation and reduction currents and ORP.

In the ORP measuring device of the present invention, in particular, since the working electrode and the base electrode of the bipolar transistor are formed integrally, the wiring for connecting the base electrode and working electrode can be omitted. This can reduce noise from outside, and enables accurate measurement of very small oxidation and reduction currents.

Namely, with the ORP measuring device of the present invention, even though the measured signal magnitude of the oxidation and reduction currents is reduced in accordance with a size reduction of the working electrode for accurate measurement of a minute object, the measured signals can be detected correctly. Also, the measurement signal can be detected correctly even if the magnitude of the measurement signal itself is weakened.

The size reduction of the ORP measuring device of the present invention enables the measuring device to be integrated in an array. Thereby, two dimensional distributions of the concentration and type of substances in a solution can be determined by measuring the oxidation and reduction currents and ORP with different array elements.

An ORP measuring device according to a second embodiment includes a rectifier circuit 36 located between the bipolar transistor 21 and the processing circuit 18 and electrically connected in parallel with the base electrode 27 and emitter electrode 28 of the bipolar transistor 21 as shown in FIG. 1, in addition to the configuration of the ORP measuring device according to the previously described embodiment. This rectifier circuit 36 is connected so as to rectify current in a direction opposite to that of the bipolar transistor. This rectifier circuit is formed by a semiconductor device that can function as a rectifier, and may be formed, for example, by a P-N junction diode 38 shown in FIG. 1, or a Schottky diode.

Since bipolar transistors show unidirectional rectifying characteristics, repeated measurements of ORP without such a rectifier circuit may accelerate either one of oxidation and reduction reactions, which may disturb the ion balance of the measured object (solution) and hinder the measurement.

With a rectifier circuit (compensation circuit) adapted to conduct current in a direction opposite to the rectifying direction of the bipolar transistor, the measured object is supplied with both the oxidation current and reduction current when the voltage applied to the counter electrode is swept during the measurement of ORP. Therefore, repeatedly measuring ORP does not disturb the ion balance and the measured object can maintain its original characteristics.

The configurations and operations of the ORP measuring devices according to this and other embodiments of the present invention, and measurement results of the ORP and current will be described with reference to the measuring devices shown in FIG. 2A to FIG. 2D and measurement results shown in FIG. 3A to FIG. 3D.

Figure 2A:
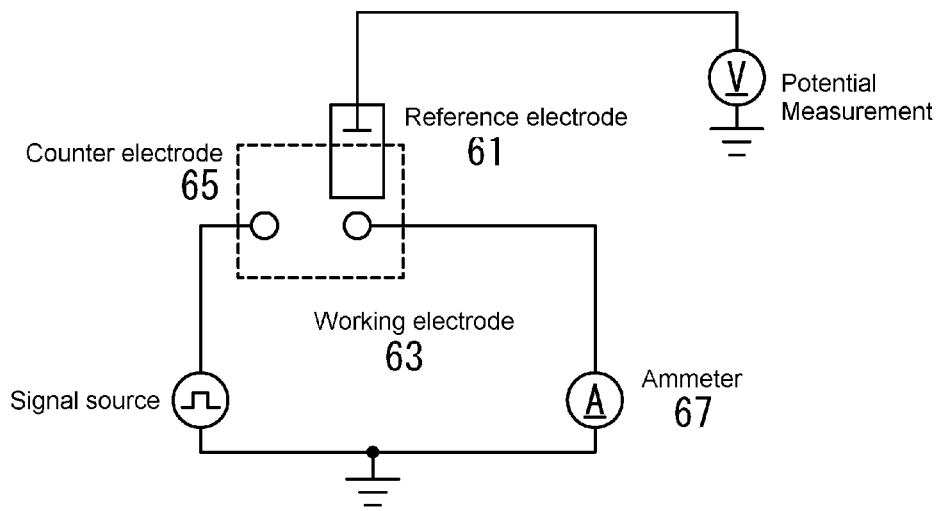
FIG. 2A is a circuit diagram illustrating a measuring device that measures ORP and current with electrodes alone.

FIG. 2A shows a common measuring device that measures ORP and current only with electrodes. The current flowing through the working electrode 63 is measured, while the potential of the liquid is monitored with the reference electrode 61. The oxidation and reduction currents flow only between the counter electrode 65 and the working electrode 63 and not through the reference electrode 61.

With the measuring device shown in FIG. 2A, the current flowing through the working electrode 63 is small when the concentration of the solution being measured is low. The current flowing through the working electrode 63 will then be affected more greatly by noise entering the circuit from external sources and by the lower end of the current range that can be measured by the ammeter 67. The measurement of the current flowing through the working electrode 63 will then be difficult, and there will be a lower end to the range of concentration of solution that can be measured. This ammeter is one example of a processing circuit.

Figure 2B:
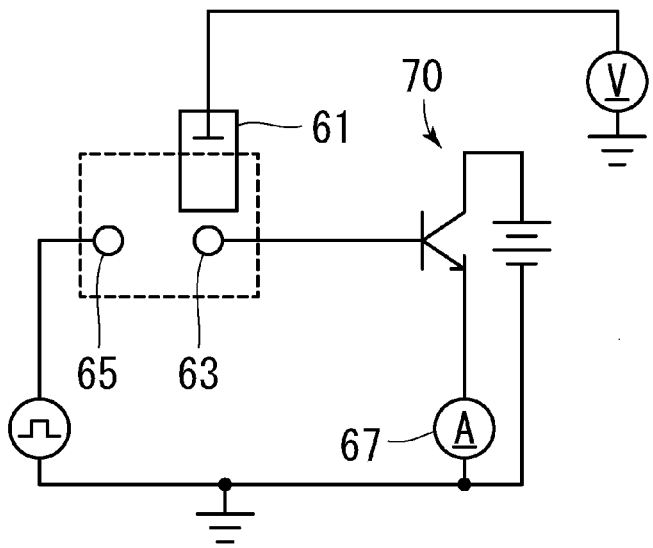
FIG. 2B is a circuit diagram illustrating a measuring device having a bipolar transistor united with a working electrode.

FIG. 2B shows the ORP measuring device according to the embodiment of the present invention in which the bipolar transistor 70, which is a current amplifying element, is united with the working electrode 63, to solve the problem described above.

In the measuring device of FIG. 2B, however, the unidirectional rectifying characteristic of the bipolar transistor 70 may accelerate either one of oxidation and reduction during the measurement, which may disturb the ion balance of the measured object.

Figure 2C:
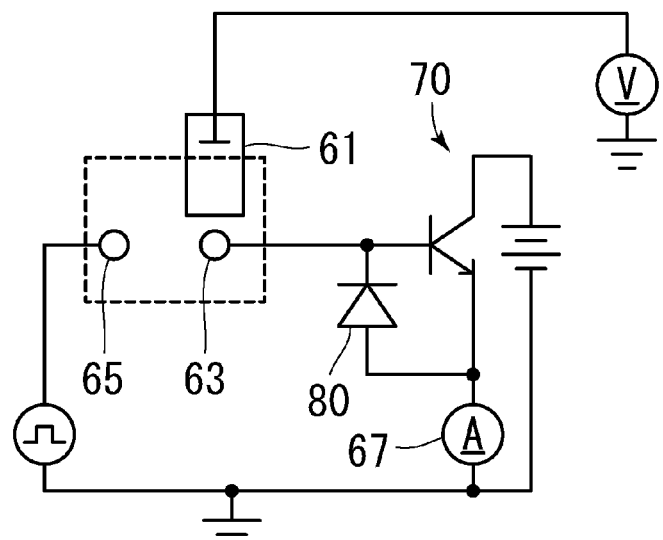
FIG. 2C is a circuit diagram illustrating a measuring device according to a second embodiment having a diode that conducts current in a direction opposite to the current flow direction of the bipolar transistor.

FIG. 2C shows an ORP measuring device according to another embodiment of the present invention in which a diode 80 that conducts current (compensation current) in a direction opposite to the current flow direction of the bipolar transistor 70 is further provided. Since the solution being measured is supplied with both the oxidation current and reduction current in the measurement circuit of FIG. 2C, ORP measurement can be carried out without changing the condition of the measured solution.

Figure 2D:
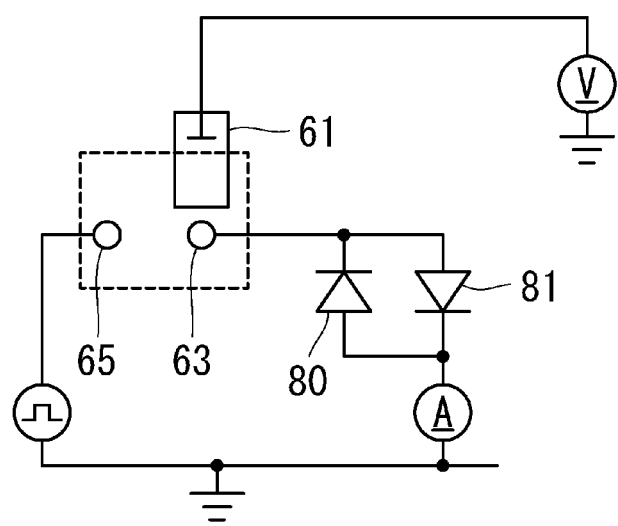
FIG. 2D is a circuit diagram illustrating a measuring device having two parallel-connected diodes that conduct current in different directions.

FIG. 2D shows, for comparison, a measuring device having two diodes 80 and 81 connected in parallel and having different rectifying directions.

Next, the measurement results obtained with the measuring devices shown in FIG. 2A to FIG. 2D will be described below. Measurement is made by CV wherein the potential of the counter electrode 65 is swept in the positive and negative directions, or by SWV wherein the potential of the counter electrode 65 is changed to create pulses.

FIG. 3A to FIG. 3D show the measurement results obtained by CV with the measuring devices shown in FIG. 2A to FIG. 2D, respectively. A 2 mM solution of potassium ferrycyanide (K3[Fe(CN)6]) was used as the measured object. The bipolar transistor used here has a current amplification factor hFE of 100, and a turn-on voltage of 0.7 V. The diode used here has a turn-on voltage of 0.5 V.

Figure 3A:
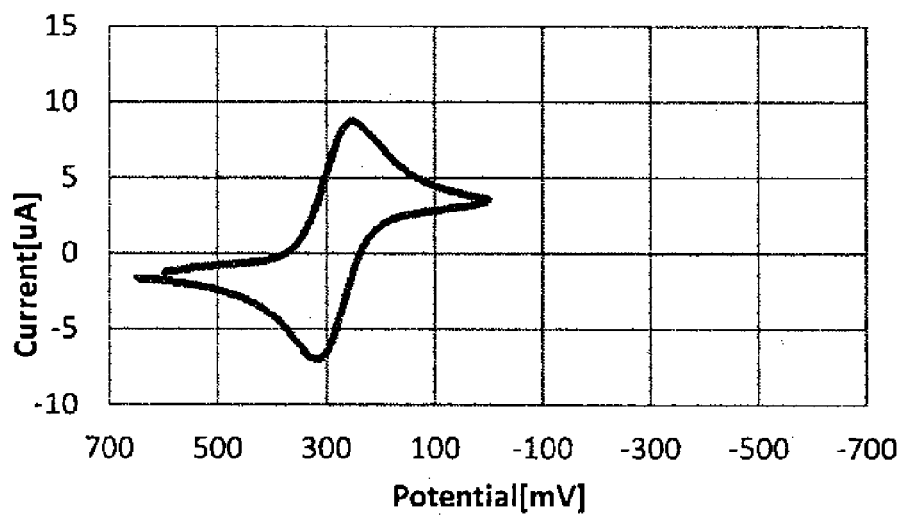
FIG. 3A is a graph showing the results of measurement made with the measuring device illustrated in FIG. 2A.
Figure 3B:
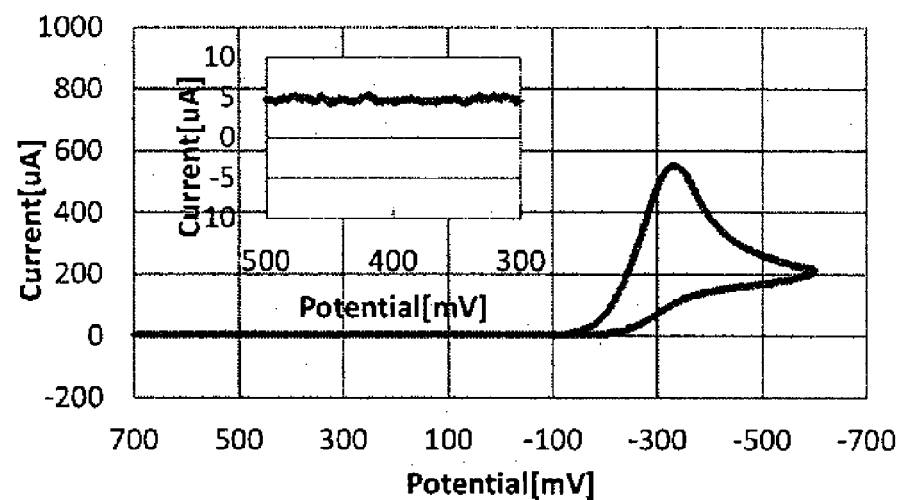
FIG. 3B is a graph showing the results of measurement made with the measuring device illustrated in FIG. 2B.

FIG. 3A shows the measurement results of the measuring device of FIG. 2A that measures the ORP and current of the working electrode 63 itself. FIG. 3B shows the measurement results of the measuring device of FIG. 2B according to the embodiment of the present invention in which the bipolar transistor is united with the working electrode.

The measurement results of FIG. 3B indicate that the current peak value is amplified about 66 times relative to the measurement results of FIG. 3A as a reference. From this, it can be understood that the bipolar transistor serves the function of the current amplifier. The negative current peak that can be found in the measurement results of FIG. 3A does not appear in the measurement results of FIG. 3B. From this, it can be understood that no oxidation current is supplied in the measured solution in the measuring device of FIG. 2B.

Figure 3C:
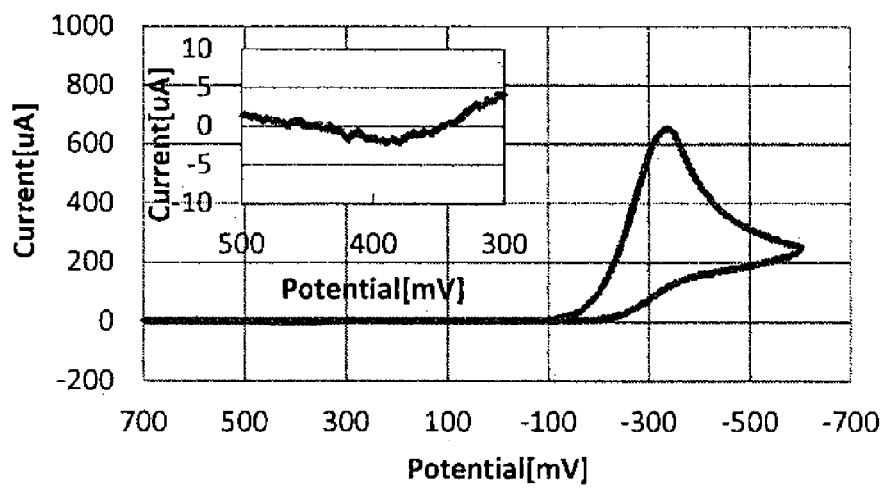
FIG. 3C is a graph showing the results of measurement made with the measuring device illustrated in FIG. 2C.

FIG. 3C shows the measurement results of the measuring device of FIG. 2C according to another embodiment of the present invention, which includes a diode 80 that conducts current in a direction opposite to the current flow direction of the bipolar transistor and that is connected in parallel with the bipolar transistor 70. From the measurement results of FIG. 3C, it can be understood that the current amplification factor is large and there is a negative current flow. Thus, with the measuring device of FIG. 2C, a measurement system in which the measured solution is supplied with both the oxidation current and reduction current can be configured.

Figure 3D:
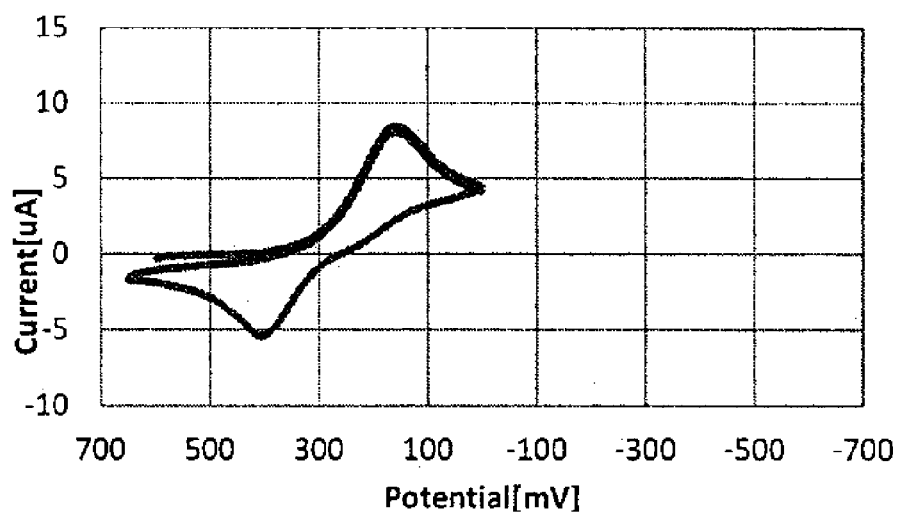
FIG. 3D is a graph showing the results of measurement made with the measuring device illustrated in FIG. 2D.

FIG. 3D shows the measurement results of a measuring device of FIG. 2D having two parallel-connected diodes 80 and 81 with different rectifying directions. A positive current peak and a negative current peak can be observed in the measurement results of FIG. 3D.

From the measurement results of FIG. 3B to FIG. 3D in comparison to those of FIG. 3A, it can be observed that the potential is shifted. This potential shift is caused by the threshold voltage of the bipolar transistor and diode added as an offset voltage. Compensating the amount of this shift enables measurement of the intrinsic ORP of the substance.

While one example of use of an NPN bipolar transistor has been described with reference to FIG. 2B and FIG. 2C, the same effects can be achieved with the use of a PNP bipolar transistor.

Figure 4A:
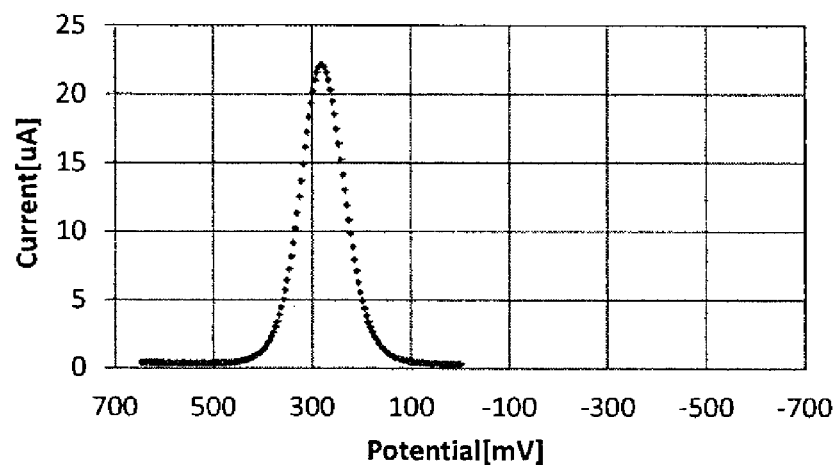
FIG. 4A is a graph showing an output waveform of the measuring device of FIG. 2A when the waveform of the voltage applied to the working electrode is changed by SWV.
Figure 4B:
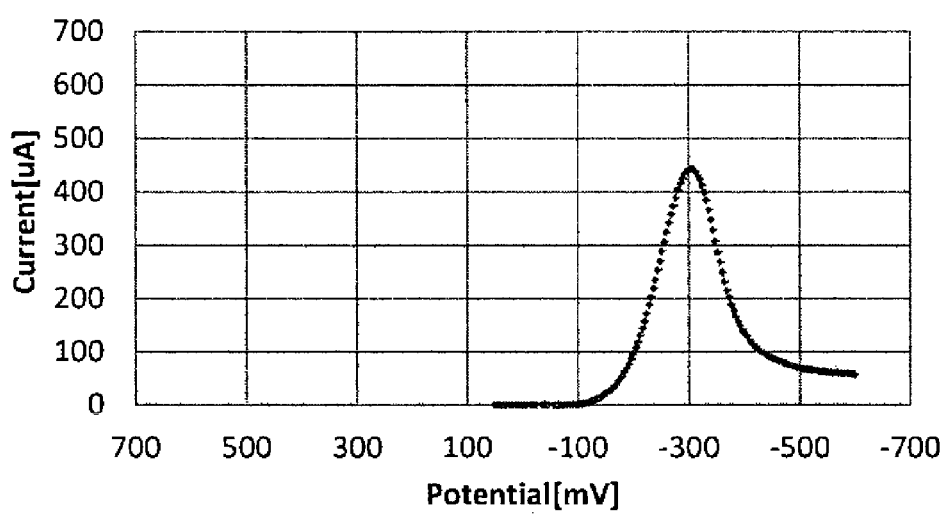
FIG. 4B is a graph showing an output waveform of the measuring device of FIG. 2C having the bipolar transistor and diode when the waveform of the voltage applied to the working electrode is changed by SWV.

FIG. 4A shows an output waveform of the measurement circuit of FIG. 2A when the waveform of the voltage applied to the counter electrode 65 is changed by SWV. FIG. 4B, on the other hand, shows an output waveform of the measuring device of FIG. 2C having the bipolar transistor 70 and diode 80 when the waveform of the applied voltage is changed by SWV. The increased peak current that can be seen in FIG. 4B indicates that the amplifying function of the bipolar transistor 70 is in action. From this, it can be understood that SWV is applicable to various ORP measurement methods that include a bipolar transistor.

Figure 5A:
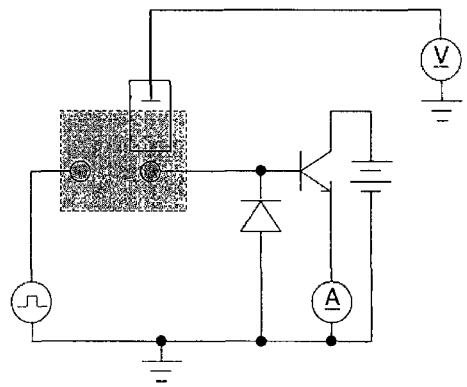
FIG. 5A is a circuit diagram illustrating a measuring device that has a bipolar transistor and measures reduction current only.
Figure 5B:
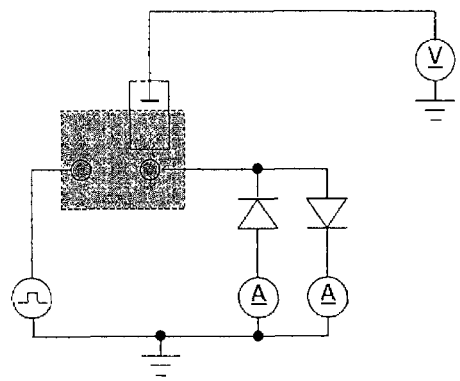
FIG. 5B is a circuit diagram illustrating a measuring device that has two diodes and measures oxidation current and reduction current separately.

Now, three types of measuring devices for measuring ORP and current will be described with reference to FIG. 5A to FIG. 5C. FIG. 5A illustrates a measuring device that has a bipolar transistor and measures only the reduction current. The measuring device shown in FIG. 5A can measure only the reduction current, as the device measures the current in series with the bipolar transistor and in parallel with the diode. FIG. 5B illustrates a measuring device that has two diodes and measures the oxidation current and reduction current separately. The measuring device shown in FIG. 5B can measure the oxidation current and reduction current separately, as the device has two parallel-connected diodes with their rectifying directions opposite to each other.

Figure 5C:
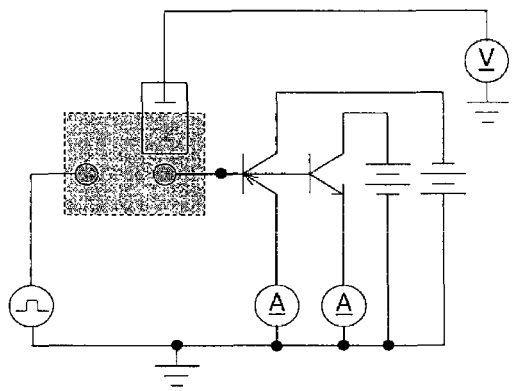
FIG. 5C illustrates a measuring device that includes two bipolar transistors for amplifying and measuring oxidation current and reduction current separately.

FIG. 5C illustrates a measuring device according to a third embodiment of the present invention that includes two bipolar transistors for amplifying and measuring the oxidation current and reduction current separately. The measuring device shown in FIG. 5C can amplify and measure the oxidation current and reduction current separately, as the device has two bipolar transistors with their base terminals connected in parallel with the working electrode. This way, the oxidation current, reduction current, and ORP can be efficiently measured without changing the condition of the measured solution.

In the ORP measuring device according to various embodiments of the present invention, voltage is applied between the counter electrode and the working electrode to measure the oxidation and reduction currents at the working electrode, and the ORP is obtained from the oxidation and reduction currents. The concentration and type of substances in the solution are then determined based on the oxidation and reduction currents and ORP.

In the ORP measuring device according to various embodiments of the present invention, in actuality, the ORP used for determining the concentration and type of the substance in the solution is not based on the oxidation and reduction currents directly measured at the working electrode, but is determined from a processed signal, which is obtained by amplifying the oxidation and reduction currents at the working electrode with the bipolar transistor and processing the amplified signal with the processing circuit.

However, the amplification factor of the bipolar transistor varies in accordance with the amount of current input to its base, because of which the output current of the working electrode is not amplified uniformly. The shape of the output waveform of the working electrode is changed by the bipolar transistor.

Therefore, in the ORP measuring device according to various embodiments, a deformation in the oxidation and reduction current characteristics that occurs during the process of amplifying the oxidation and reduction currents is corrected in consideration of the amplification characteristics of the bipolar transistor.

Figure 6:
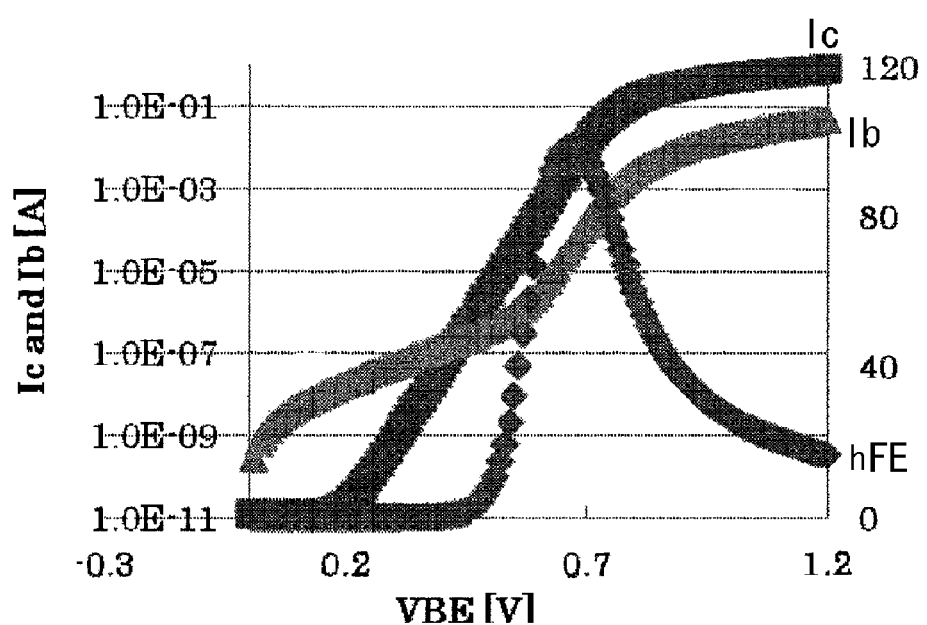
FIG. 6 is a graph showing the output characteristics of a bipolar transistor.

FIG. 6 shows the amplification characteristics of a bipolar transistor in one exemplary embodiment. FIG. 6 indicates that the current amplification factor hFE is affected by both the base emitter voltage VBE represented by the horizontal axis and the base current Ib represented by the vertical axis. It can be seen, in particular, that the current amplification factor hFE is largely affected by a change in the base current Ib.

Therefore, for carrying out the correction noted above, the current amplification factor hFE of each output from the bipolar transistor is specified based on the base emitter voltage VBE and the base current Ib. Since the current output from the working electrode varies, the amplification factor of the bipolar transistor changes accordingly. Therefore, the current value of the output waveform of the bipolar transistor should preferably be corrected such that the difference between an obtained current amplification factor and a predetermined current amplification factor (e.g., maximum amplification factor) is compensated.

The voltage value of the output waveform of the bipolar transistor, on the other hand, is affected by a voltage shift caused by the connection of the bipolar transistor and diode. Therefore, this voltage shift may be corrected.

Figure 7A:
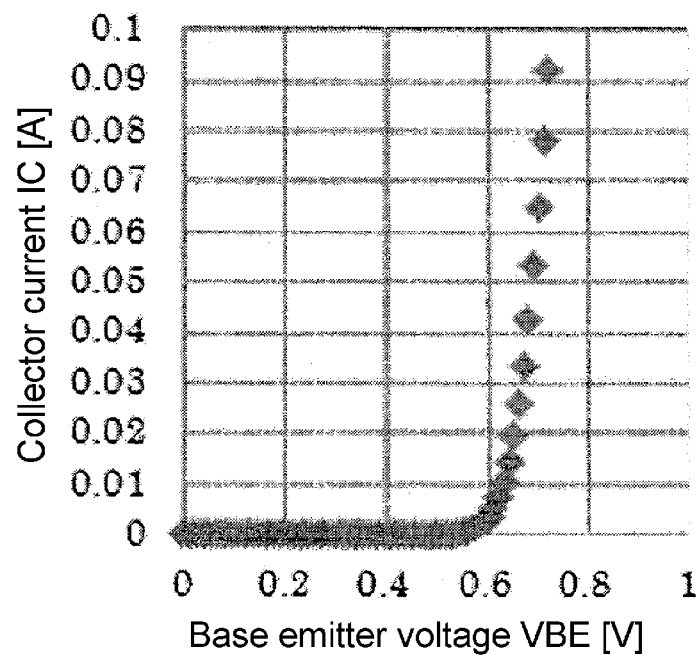
FIG. 7A is a graph showing the threshold characteristics of a bipolar transistor.
Figure 7B:
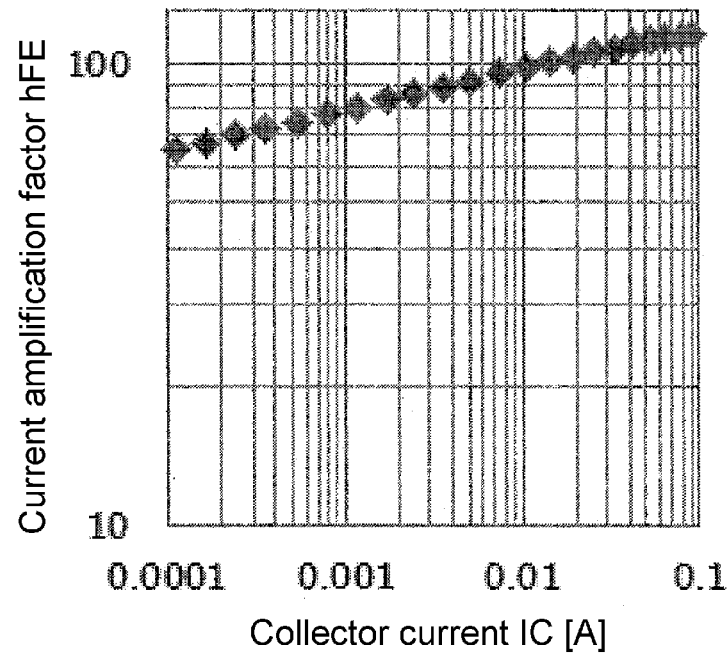
FIG. 7B is a graph showing the hFE of the bipolar transistor.

FIG. 7A shows the threshold characteristics of the bipolar transistor, and FIG. 7B shows the current amplification factor hFE of the bipolar transistor. As shown in FIG. 7A, the bipolar transistor has a threshold of current amplification factor hFE of about 0.6 V. On the other hand, the amount of shift in FIG. 3B relative to FIG. 3A as a reference is about 0.57 V. Thus the threshold of the bipolar transistor is matched very well by the shift amount in FIG. 3B.

The bipolar transistor amplifies current about 92 times, on average. On the other hand, the oxidation current in FIG. 3B is amplified about 66 times. This difference is attributable to the fact that current amplification takes place only around the threshold because the potential of the solution is kept constant by the reference electrode so that voltage of equal to or more than the threshold of the bipolar transistor is not applied. The current amplification factor hFE around the threshold is about 70 times.

To correct the deformation of the output waveform of the bipolar transistor to return it back by division to the output waveform of the working electrode itself, the following formulas are executed:

Oxidation potential=(Potential at which the bipolar transistor is held)+(Base emitter $V_{BE}$)

Oxidation current=(Output current of the bipolar transistor)÷(Current amplification factor $hFE$)

Figure 8:
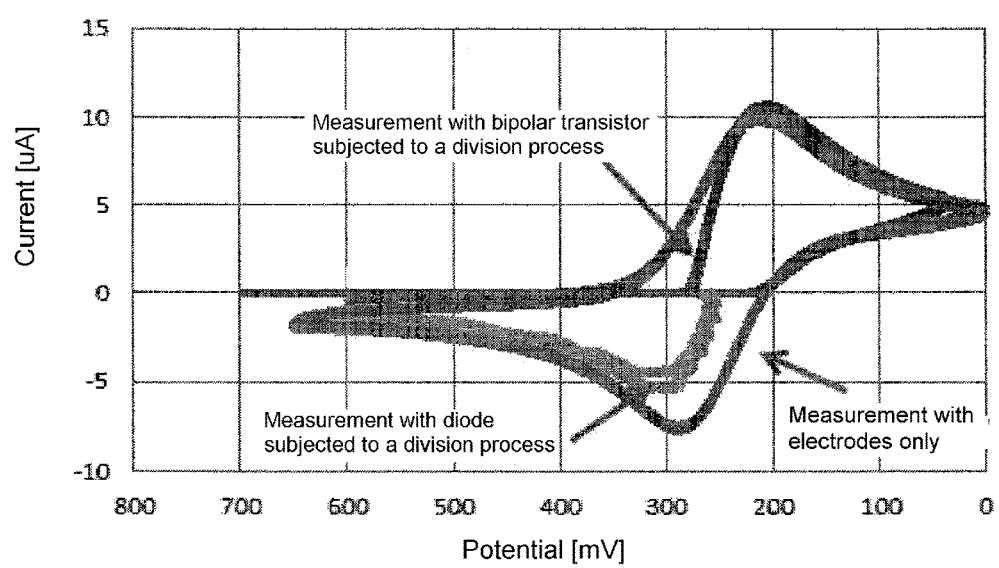
FIG. 8 is a graph showing the measurement results of voltage and current measured with electrodes only, voltage and current measured with a bipolar transistor and subjected

FIG. 8 shows both the output waveform of the working electrode itself and a waveform obtained as the result of the division calculation above. Generally, in view of the fact that the characteristics of the object being measured are specified from the peak voltage, it is understood that the peak voltage of the waveform obtained by the division process matches the peak voltage of the output waveform of the working electrode itself.

Accordingly, the peak voltage can be specified correctly by amplifying a small output (current) of the measured object without noise and obtaining an original waveform through the division mentioned above.

Figure 9A:
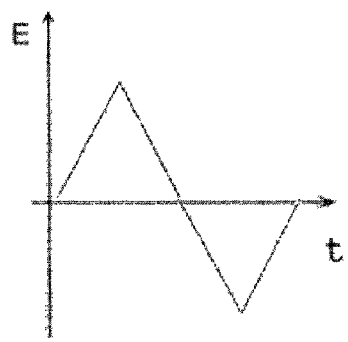
FIG. 9A is a waveform chart showing a waveform of voltage applied by CV.
Figure 9B:
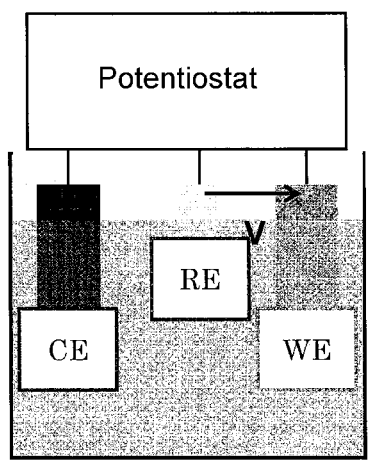
FIG. 9B is a schematic diagram illustrating a configuration of applying voltage to the electrode by CV.
Figure 9C:
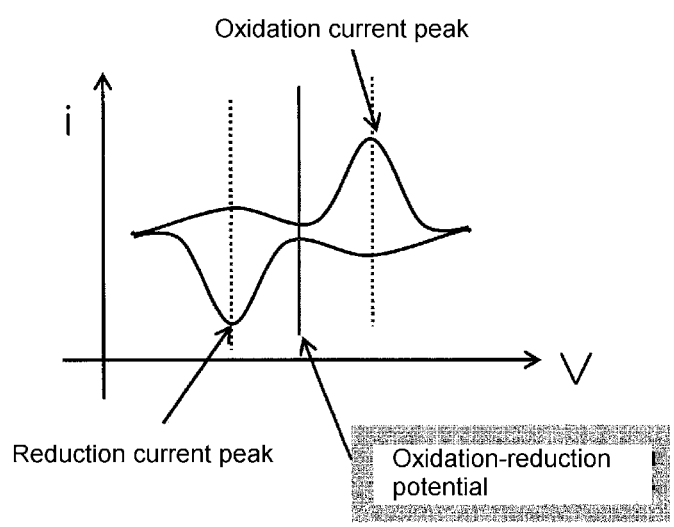
FIG. 9C is a graph showing the relationship between the applied voltage measured by CV and the oxidation and reduction currents.

FIG. 9A shows the voltage applied by CV, FIG. 9B illustrates a configuration of applying voltage to the electrode by CV, and FIG. 9C shows the relationship between the applied voltage measured by CV and the oxidation and reduction currents.

In CV, voltage shown in FIG. 9A is applied across the counter electrode and working electrode in the electrode configuration shown in FIG. 9B. Voltage is then swept to positive and negative directions so that oxidation and reduction currents are detected. FIG. 9C shows the detection results. From the relationship between the applied voltage and the oxidation and reduction currents shown in FIG. 9C, a reduction current peak and an oxidation current peak are obtained, from which the ORP is determined. The concentration of the substance in the solution is determined from the reduction current peak and oxidation current peak, and the substance is identified based on the ORP.

Measurement by CV takes time because of charging of the electrical double layer that is formed by a capacitor component between the electrode and the container. To shorten the measurement time, it is necessary to reduce the capacitor component by making the electrode and container smaller. Reducing the size of the electrode, however, also leads to the problem of reduction in the detected oxidation and reduction currents. However, the ORP measuring device of the present invention can detect the oxidation and reduction currents and ORP accurately with the use of the bipolar transistor even though the detectable oxidation and reduction currents are reduced, and thereby can solve the problem.

Figure 10A:
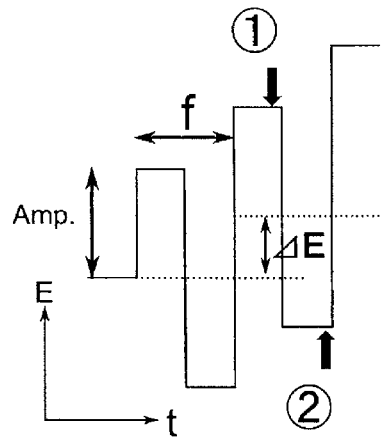
FIG. 10A is a waveform chart showing a waveform of voltage applied by SWV.
Figure 10B:
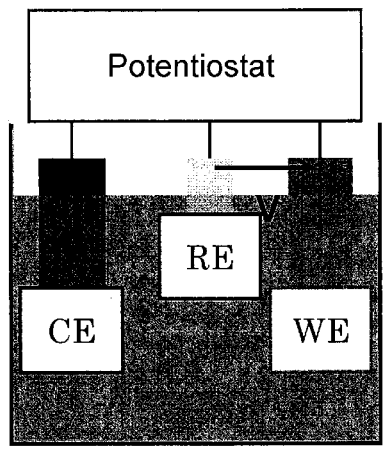
FIG. 10B is a schematic diagram illustrating a configuration of applying voltage to the electrode by SWV.
Figure 10C:
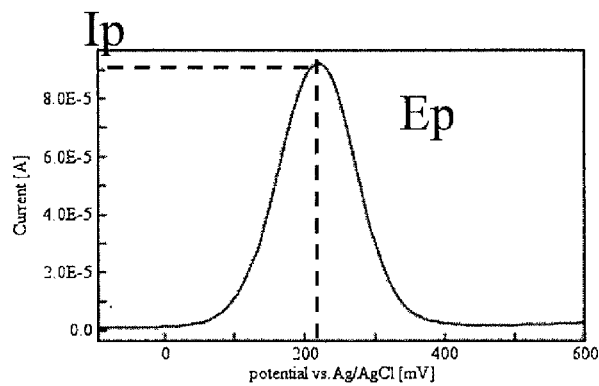
FIG. 10C is a graph showing the relationship between the working electrode potential measured by SWV and the current difference value relative to the working electrode potential.

FIG. 10A shows the voltage applied by SWV, FIG. 10B illustrates a configuration of applying voltage to the electrode by SWV, and FIG. 10C shows the relationship between the working electrode potential measured by SWV and the current difference value relative to the working electrode potential.

In SWV, pulsed voltage shown in FIG. 10A is applied between the counter electrode and the working electrode in the electrode configuration shown in FIG. 10B. The potential at the working electrode and the current difference value relative to the working electrode potential are detected. FIG. 10C shows the detection results. The concentration of the substance in the solution can be determined from the peak current difference value shown in FIG. 10C. ORP is obtained from the peak current difference value and the corresponding potential, and thus the substance in the solution is specified from the ORP. Namely, by SWV, the concentration and type of the substance are determined directly from the relationship between the working electrode potential and the current difference value relative to the working electrode potential shown in FIG. 10C.

With CV, the measurement speed can only be increased to a limited extent because of the electrical double layer formed by a capacitor component between the electrode and the container. Also, the speed increase makes noise larger than the measurement signal, which may make the measurement impossible. With SWV, on the other hand, the capacitor component between the electrode and the container is rapidly charged by application of pulsed voltage, so that the measurement can be carried out at higher speed as compared to CV. SWV is also advantageous in high speed measurement, as noise can be reduced with SWV. Generally, increasing the speed of measurement slightly increases the measured signal, which, however, is not enough to improve the measurement performance High speed measurement with SWV is effective with the structure of this embodiment.

Figure 11:
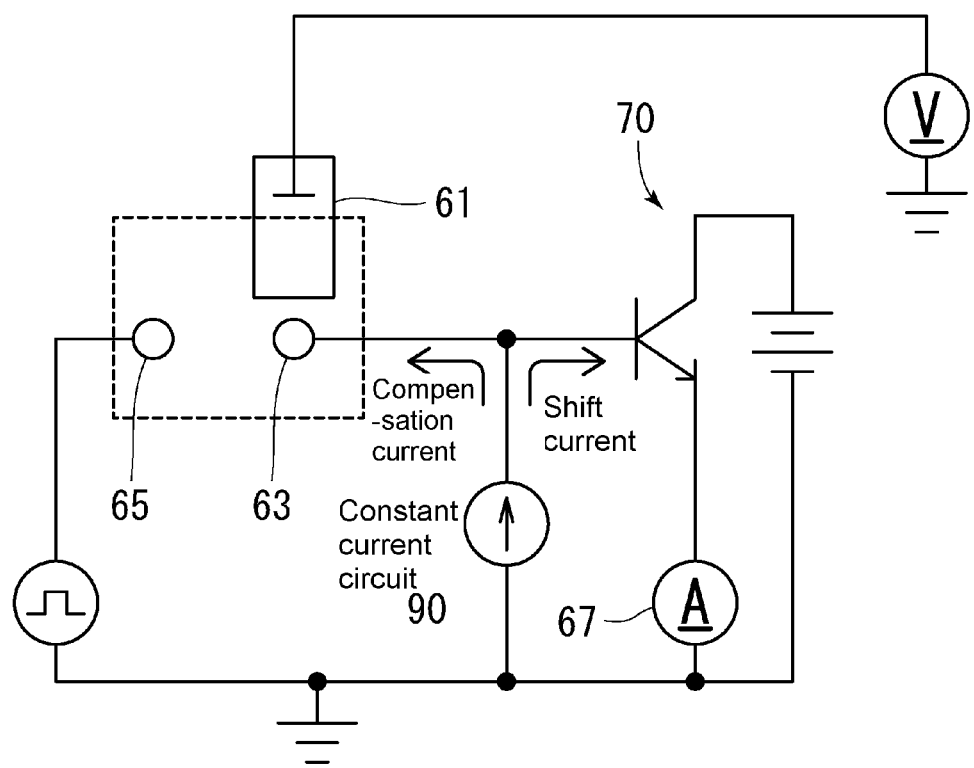
FIG. 11 is a circuit diagram of a measuring device in another embodiment.

FIG. 11 shows a circuit diagram of a measuring device in another embodiment of this invention. In FIG. 11, same elements as those in FIG. 2 are given the same reference numerals and will not be described.

In this measuring device, a constant current circuit 90 is provided, so that a constant current is applied between the working electrode 63 and the base of the bipolar transistor 70. This constant current circuit 90 need not be provided on the substrate where the working electrode 63, bipolar transistor 70, and ammeter 67 that is the processing circuit are arranged, but may be provided on another substrate, with its output terminal being connected to the base of the working electrode 63. Similarly, the ammeter 67 may be arranged on another substrate.

Even when the rectifying function of the bipolar transistor 70 is in action, a compensation current is applied from the constant current circuit 90 to the working electrode 63, so that an oxidation reaction and a reduction reaction always occur at the measured object.

The output current of the constant current circuit 90 is made sufficiently larger than the output current of the working electrode 63 (e.g. 100 times or more), and set close to the peak of the hFE curve of the bipolar transistor 70 shown in FIG. 6. Thereby, the current amplification factor hFE of the bipolar transistor 70 is maintained substantially constant, even though the output of the working electrode 63 is superimposed on the output of the constant current circuit 90.

The current amplification factor hFE of the bipolar transistor 70 is also affected by a change in the base emitter voltage, which, however, is negligible, as compared to the influence caused by the logarithm of a base current change.

Therefore, the output of the bipolar transistor 70 hardly changes the output waveform of the working electrode 63 itself.

FIG. 12A to FIG. 12D show waveforms in various parts of the measuring device of FIG. 11.

Figure 12:
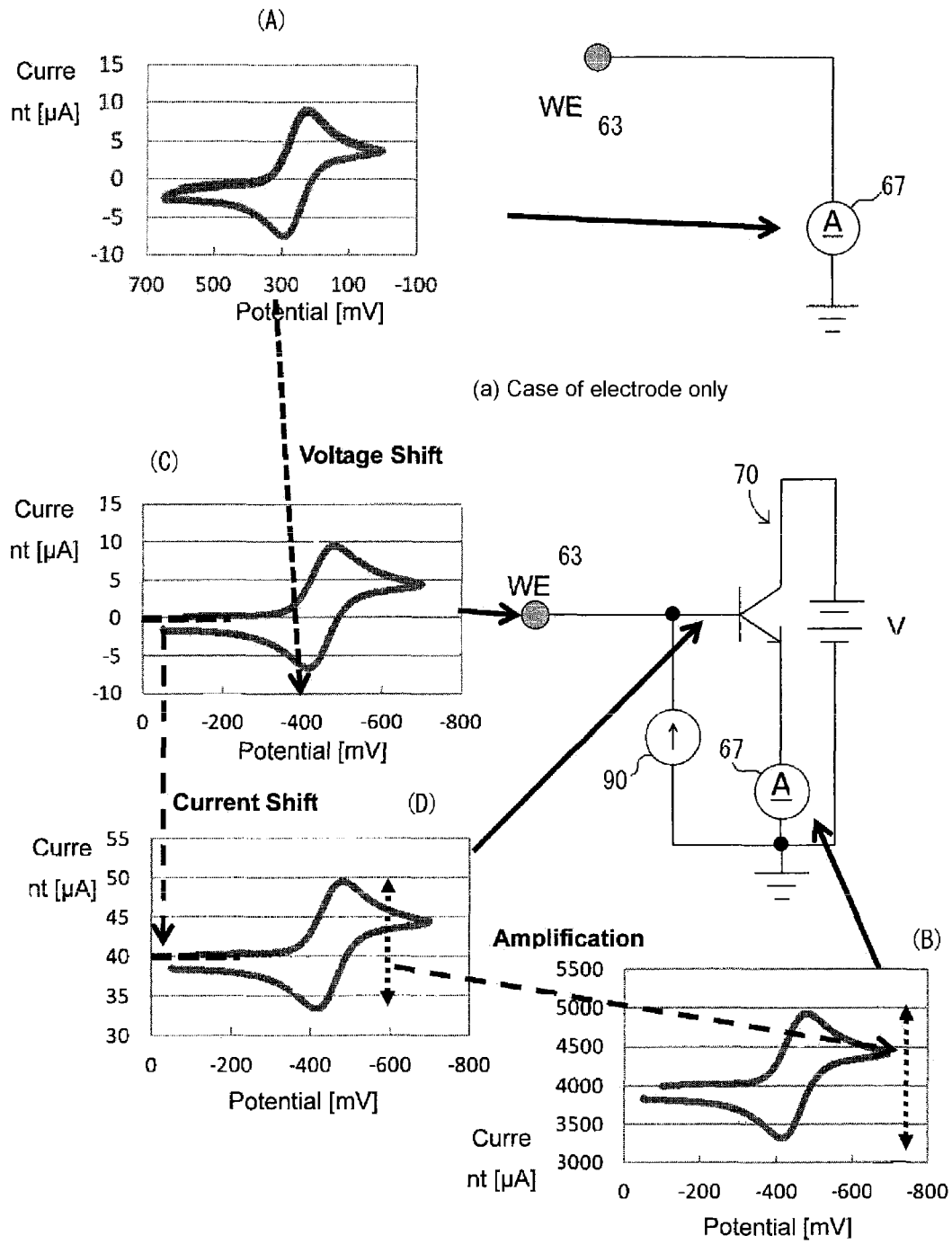
FIG. 12 is a schematic diagram for explaining the operation of the measuring device illustrated in FIG. 11.

FIG. 12A shows a waveform of the output of the working electrode 63 itself.

FIG. 12B shows an output waveform of the bipolar transistor 70.

FIG. 12C shows a waveform with a voltage shift caused by the constant current circuit 90 and bipolar transistor 70.

FIG. 12D shows a waveform of the current flowing to the base in the shifted state.

From the illustration diagrams of FIG. 12A to FIG. 12D, it is understood that the output waveform of the working electrode 63 itself becomes the output waveform of the bipolar transistor 70 without being deformed in any way and that the peak voltage of the latter waveform reduced by division matches the peak voltage of the output waveform of the working electrode 63 itself.

Figure 13:
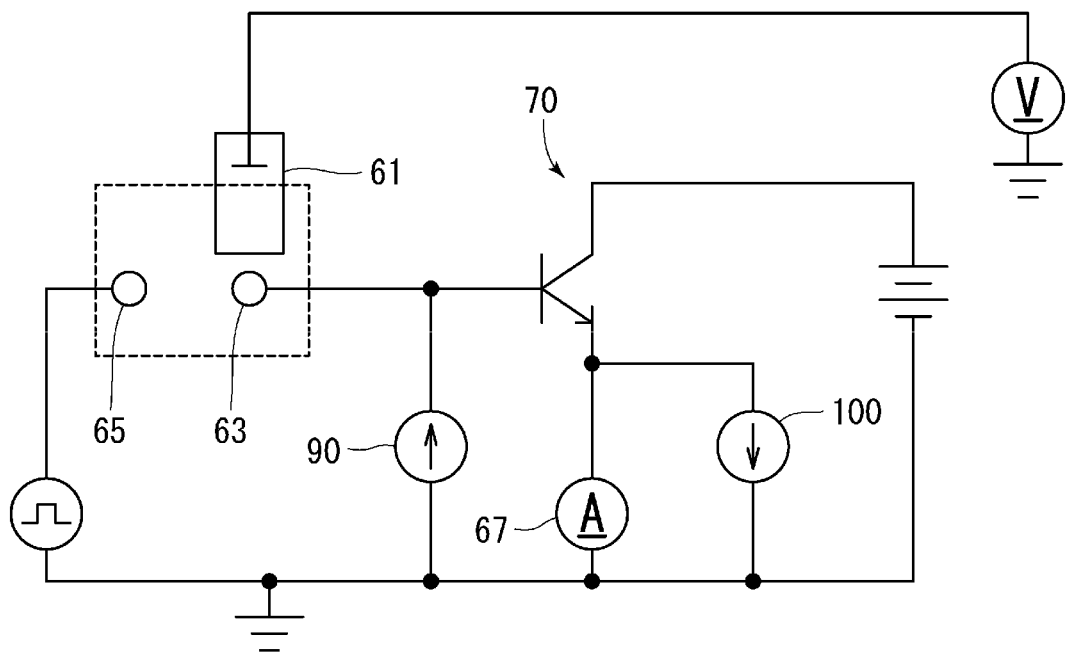
FIG. 13 is a circuit diagram illustrating a variation of the measuring device illustrated in FIG. 11.

The output current of the bipolar transistor 70 contains a component of the shift current applied by the constant current circuit 90. As a result, the ratio of a change in the output current of the working electrode 63 to the entire current is reduced. Therefore, it is preferable to provide a current removal circuit 100, as shown in FIG. 13, to remove the influence of the shift current. This current removal circuit 100 should multiply the shift current with the current amplification factor hFE. Thereby, the ammeter can have high sensitivity.

In FIG. 13, same elements as those in FIG. 11 are given the same reference numerals and will not be described.

Figure 14:
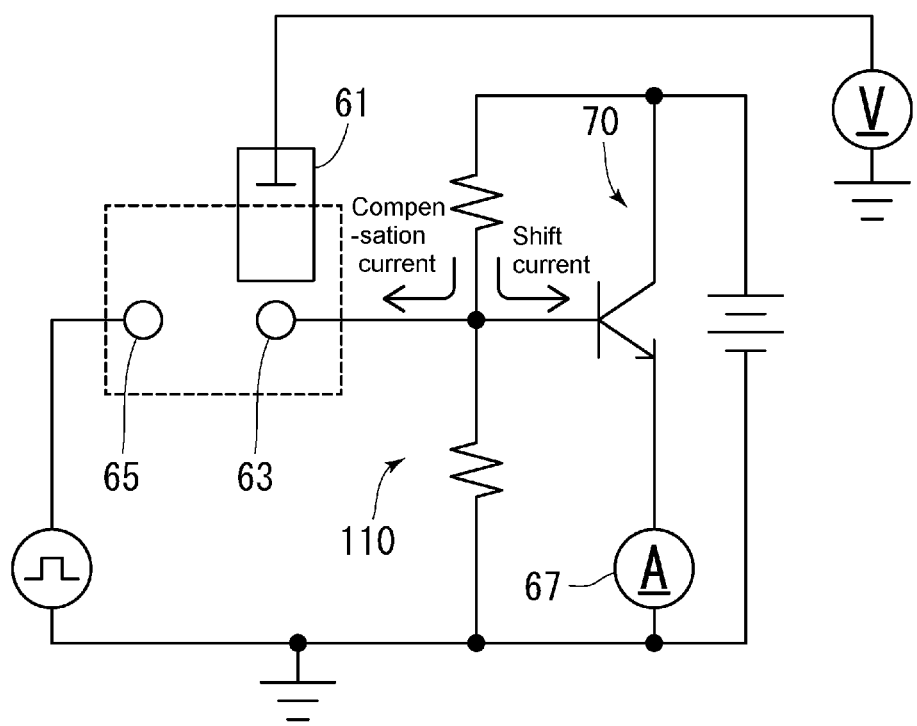
FIG. 14 shows a circuit of a measuring device in another embodiment.

FIG. 14 shows a circuit diagram of a measuring device in another embodiment. In FIG. 14, same elements as those in FIG. 13 are given the same reference numerals and will not be described.

In this measuring device, a constant voltage circuit 110 is connected to the working electrode 63 and the base of the bipolar transistor 70. This constant voltage circuit 110 need not be provided on the substrate where the working electrode 63, bipolar transistor 70, and ammeter 67 that is the processing circuit are arranged, but may be provided on another substrate, with its output terminal being connected to the base of the working electrode 63.

Even when the rectifying function of the bipolar transistor 70 is in action, a compensation current is applied from the constant voltage circuit 110 to the working electrode 63, so that an oxidation reaction and a reduction reaction always occur at the object being measured.

The output current of the constant voltage circuit 90 is made sufficiently larger than the output current of the working electrode 63 (e.g. 100 times or more), and set close to the peak of the hFE curve of the bipolar transistor 70 shown in FIG. 6. Thereby, the current amplification factor hFE of the bipolar transistor 70 is maintained substantially constant, even though the output of the working electrode 63 is superimposed on the output (shift current) of the constant voltage circuit 110.

This invention shall not be limited by the description of embodiments and examples of the invention above in any way. The invention includes various modified forms that can readily be conceived by a person skilled in the art without departing from the scope of the claims.

REFERENCE SIGNS LIST

10: Substrate
11: Measurement unit
12: Container
15, 63: Working electrode
18: Signal processing circuit
21, 70: Bipolar transistor
23: Collector region
24: Base region 25: Emitter region
26: Collector electrode
27: Base electrode
28: Emitter electrode
36: Semiconductor device having a rectifying function
38: PN junction diode
61: Reference electrode
65: Counter electrode
67: Ammeter
80, 81: Diode
90: Constant current circuit
100: Current removal circuit
110: Constant voltage circuit

The invention claimed is:

1. A device for measuring oxidation-reduction potential, comprising:
    a substrate;
    a working electrode formed on a surface of the substrate;
    a processing circuit that processes an output of the working electrode;
    wherein the substrate is provided with a bipolar transistor for amplifying the output of the working electrode, and further comprising a compensation circuit that applies a compensation current to the working electrode in a direction opposite to that of a current applied from the working electrode to the bipolar transistor.

2. The measuring device according to claim 1, wherein the compensation circuit includes a constant current circuit or a constant voltage circuit for shifting the current applied from the working electrode to a base of the bipolar transistor so that the bipolar transistor has a constant amplification factor.

3. The measuring device according to claim 1, wherein the compensation circuit is a rectifying semiconductor element arranged in parallel with the bipolar transistor between the working electrode and the processing circuit.

4. The measuring device according to claim 1, wherein said device is configured to convert an output of the bipolar transistor to a shape identical to that of the output of the working electrode.

5. The measuring device according to claim 1, wherein a first doped region doped to be a first conductor type to form a collector region of the bipolar transistor, a second doped region doped to be a second conductor type within the first doped region to form a base region of the bipolar transistor, and a third doped region doped to be the first conductor type within the second doped region to form an emitter region of the bipolar transistor, are formed on the substrate, and wherein the working electrode is stacked upon the base region exposed on a surface of the substrate.

6. A method of measuring oxidation-reduction potential that uses a measuring device including a substrate, a working electrode arranged in a container formed on a surface of the substrate, a processing circuit that processes an output of the working electrode, and a bipolar transistor formed on the substrate to amplify the output of the working electrode, the measurement method comprising the steps of:
    applying a sweeping voltage to a counter electrode arranged opposite to the working electrode inside the container;
    amplifying a current output from the working electrode with the bipolar transistor before the current is applied to the processing circuit; and
    producing a compensation current that flows in a direction opposite to that of a current output from the working electrode to a base of the bipolar transistor in a case where a first potential is applied to the counter electrode, when a second potential different from the first potential is applied to the counter electrode.

7. The measurement method according to claim 6, further comprising the step of applying a shifting current to the current output from the working electrode to the base of the bipolar transistor so that the bipolar transistor has a constant amplification factor.

* * * * *